United States Patent [19]

Ciarlei

[11] Patent Number: 5,314,070
[45] Date of Patent: May 24, 1994

[54] CASE FOR FLEXIBLE BORESCOPE AND ENDOSCOPE INSERTION TUBES

[75] Inventor: Joseph A. Ciarlei, Marcellus, N.Y.

[73] Assignee: Welch Allyn, Inc., Skaneateles Falls, N.Y.

[21] Appl. No.: 991,135

[22] Filed: Dec. 16, 1992

[51] Int. Cl.⁵ .............................. B65D 85/04
[52] U.S. Cl. ..................... 206/570; 53/430; 53/473; 206/363; 206/408; 242/172
[58] Field of Search .............. 53/430, 473; 206/363, 206/389, 391, 395, 396, 397, 408, 438, 570; 242/172

[56] References Cited

U.S. PATENT DOCUMENTS

| | | | |
|---|---|---|---|
| 1,401,904 | 12/1921 | Griffin | 206/397 |
| 2,180,858 | 11/1939 | Bedell | 206/408 |
| 2,652,922 | 9/1953 | Schweich | 206/396 |
| 3,417,867 | 12/1968 | Kahn | 206/408 |
| 3,587,840 | 6/1971 | Hultberg | 206/408 |
| 4,116,338 | 9/1978 | Weichselbaum | 206/438 |
| 4,256,225 | 3/1981 | Jackson | 206/363 |
| 4,529,148 | 7/1985 | Hesprich et al. | 206/389 |
| 4,572,370 | 2/1986 | Cedenblad et al. | 206/408 |
| 4,607,746 | 8/1986 | Stinnette | 242/172 |
| 4,853,774 | 8/1989 | Danna et al. | |
| 5,163,554 | 11/1992 | Lampropoulos et al. | 206/391 |

FOREIGN PATENT DOCUMENTS

| | | | |
|---|---|---|---|
| 2368860 | 6/1978 | France | 206/396 |
| 0772636 | 4/1957 | United Kingdom | 206/363 |

*Primary Examiner*—Jimmy G. Foster
*Attorney, Agent, or Firm*—Harris Beach & Wilcox

[57] ABSTRACT

A shipping and storage case for a borescope or endoscope has a coil of a tubular low-friction material, such as PVC tubing, to receive the borescope's flexible insertion tube. The coil can be in a form of a flat spiral positioned adjacent one side wall of the shell, or in the form of a helical spiral positioned adjacent the side walls within the case. The coil of tubing provides a convenient way for insertion tubes to be packaged and protected during shipping and storage.

13 Claims, 3 Drawing Sheets

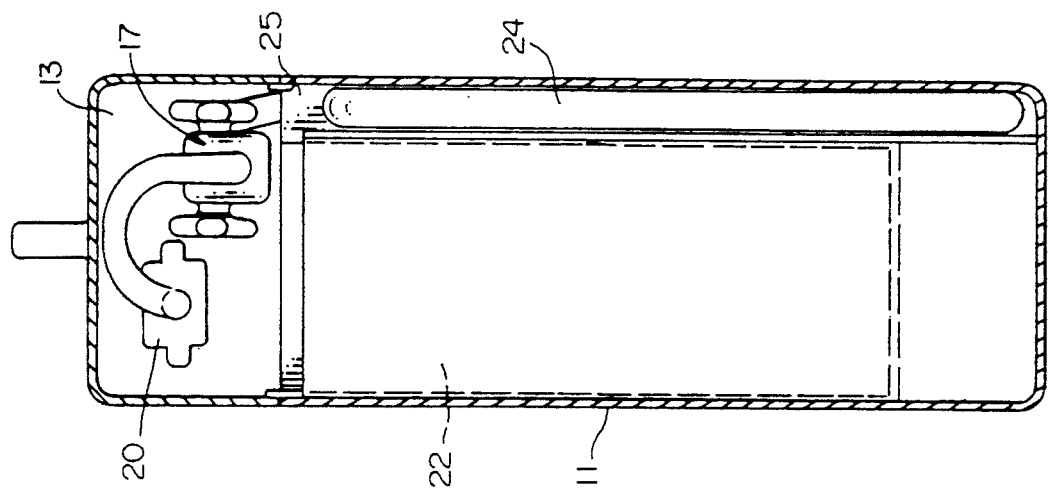
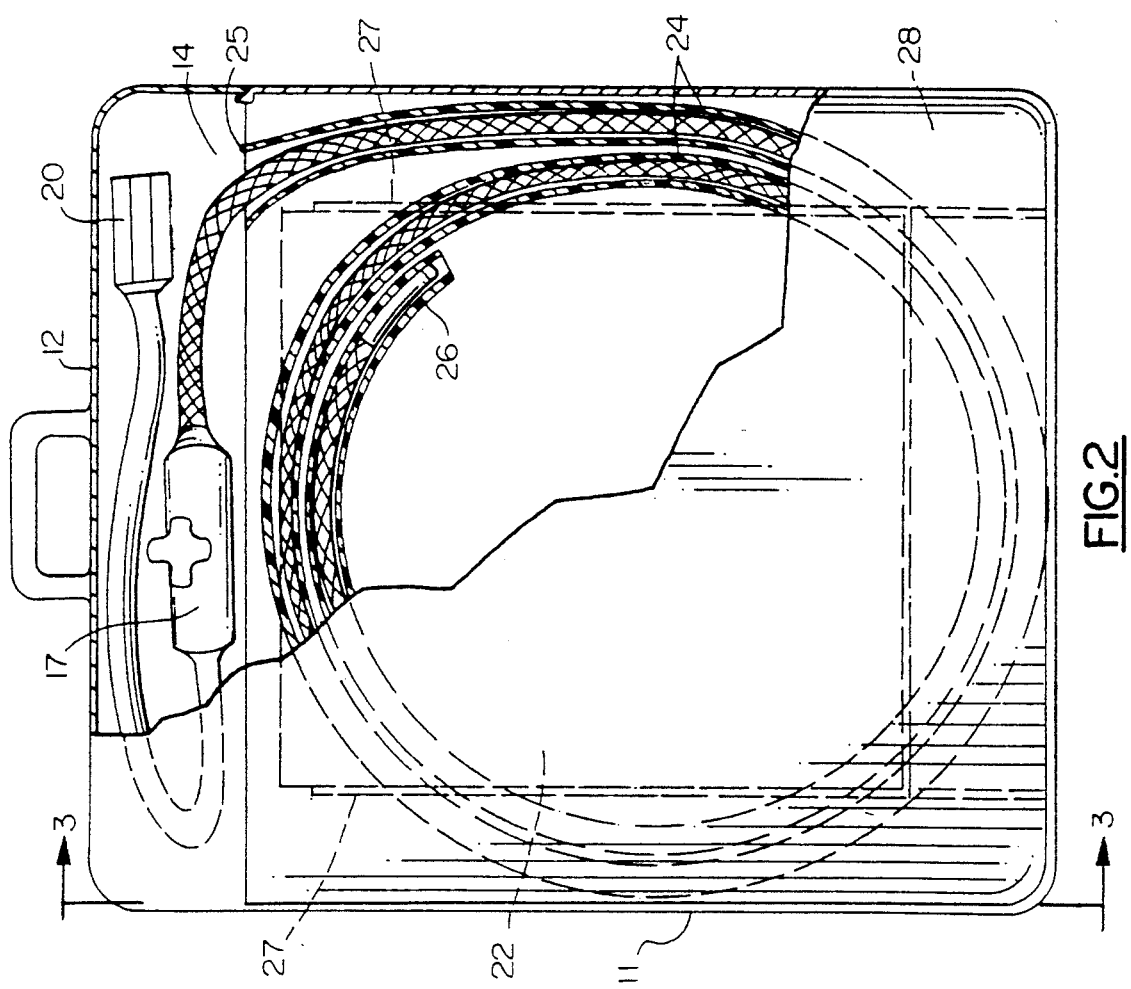

CASE FOR FLEXIBLE BORESCOPE AND ENDOSCOPE INSERTION TUBES

BACKGROUND OF THE INVENTION

This invention relates to shipping and storage containers, especially for storing elongated flexible tubular probes of the type which can contain delicate or expensive mechanisms therewithin. Borescopes, endoscopes, or other similar probes typically have an elongated flexible insertion tube with an imaging device carried on its distal tip for the purpose of capturing the image of a target object within the viewing field of the borescope. In a so-called fiberscope, a coherent fiber optic bundle carries the image to a viewing device at the proximal end of the insertion tube. In a video scope, a miniature video camera is disposed at the end of the flexible elongated insertion tube, and video images are carried over conductors which extend through the tube to its proximal end. In either case, illumination is carried on a fiber optic bundle to the distal end of the insertion tube to illuminate the remote target. Also, in either case, sensitive and delicate focussing optics are carried at the distal tip. A steering mechanism, which can be a stack of disks separated by beads or spacers, articulates the distal end of the insertion tube for purposes of steering and positioning of the imaging device. Steering cables within the insertion tube connect the steering section with a control section at the proximal end.

For purposes of transport or storage between uses, the borescope insertion tube is stored in a box or case filled with open cell or closed cell foam padding. Typically, an annular cutout is formed in the foam, and the insertion tube is laid in the cutout for storage. Other parts of the borescope are stored in other recesses and receptacles in the foam filling. Then, the lid of the case is closed, and the delicate parts of the insertion tube are protected from abuse or shock. However, in some cases, the insertion tube is not completely contained within the case when the lid is shut. If part of the insertion tube extends over the lip of the case when the lid is closed, the sheath of the insertion tube can be inadvertently crushed when the user closes the case. This damage often requires expensive repairs, which must be conducted at the factory. The numerous cables, fiber optic bundles, optics, and electrical conductors can be damaged or severed if the insertion tube is not properly positioned in the foam padding when the lid is closed.

OBJECTS AND SUMMARY OF THE INVENTION

Accordingly, it is an object of this invention to position an insertion tube within a storage and/or shipping case so as to ensure its proper positioning within the case and to protect the insertion tube while preventing inadvertent crushing of the insertion tube.

It is another object of this invention to provide a simple and reliable storage and transport case structure.

It is a further object to provide a storage and shipping case which avoids the drawbacks of the prior art.

In accordance with an aspect of this invention, a shipping and storage case for a borescope or endoscope has a shell or housing, and a coil of tubular low-friction material positioned within it. Preferably, this coil can include a flat spiral of polyvinyl chloride (PVC) tubing which has a slightly larger inside diameter than the outer diameter of the insertion tube. The spiral of PVC tubing is then disposed adjacent one side wall of the shell. The coil has sufficient length to contain the associated insertion tube.

For storage, the distal end of the insertion tube is inserted into an open proximal end of the coil of tubing and the insertion tube is slid in for storage. The case has a compartment for storage of the power supply and video monitor unit, and other receptacles, for example, for the steering control section and modular connectors at the proximal end of the insertion tube.

Preferably, the shell of the case can be formed without requiring open cell or closed cell foam. This permits use of the borescope without having to remove the video monitor and power supply unit from the case, because the heat-retaining foam is not employed. Also, the tubular coil take any of various forms, such as a flat spiral or a helix, depending on the design of the case.

The above and many other objects, features, and advantages of this invention will become apparent from the ensuing description of the preferred embodiment, which should be read in conjunction with the accompanying drawing.

BRIEF DESCRIPTION OF THE DRAWING

FIG. 2 is a front elevation of the case, partly cut away, showing details of the tubular storage coil.

FIG. 3 is a side elevation, partly cut away, taken at 3—3 of FIG. 2.

DETAILED DESCRIPTION OF THE PREFERRED EMBODIMENT

Figure 1:
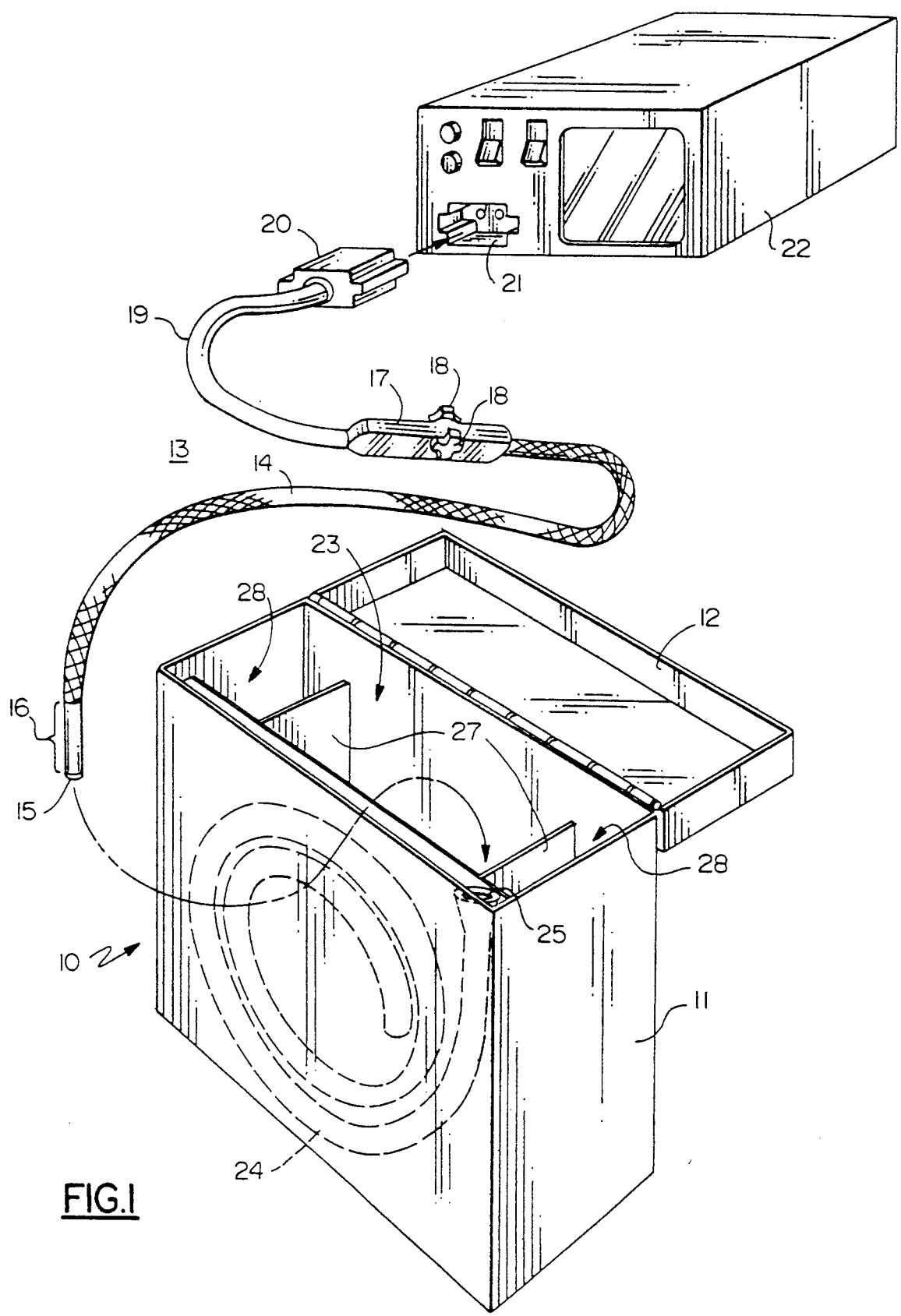
FIG. 1 is a perspective view of a borescope and its associated storage and shipping case, according to one embodiment of this invention.

With reference to the drawing, and initially to FIG. 1 thereof, a shipping or storage case 10 for a borescope is formed of a shell or housing 11 with a lid 12 connected to it by a hinge. An associated borescope 13 has an elongated flexible insertion tube 14, in this case of the video type, having a miniature video camera 15 disposed at a distal tube end of the tube 14. A steering section 16 is incorporated proximally of the camera 15 and is connected by steering cables which pass proximally, through the interior of the insertion tube, to a control section 17 positioned at the proximal end of the flexible insertion tube. In this embodiment a pair of steering knobs 18 control up-and-down and left-and-right movement of the steering section 16.

A flexible umbilical 19 extends proximally from the steering section to a connector module 20 which, in this embodiment, contains video processing circuitry. The module 20 fits into a socket or receptacle 21 in a video monitor unit 22. The unit 22 also includes a power supply for supplying dc power to the electronics within the connector module 20 and a light source for providing illumination which is conducted by a fiber optic bundle that extends through the modular connector, and thence through the umbilical 19 and insertion tube 14 to the distal tip of the insertion tube. This provides light for illuminating the target area in advance of the camera 15.

A receptacle 23 is formed in the case 10 to receive the monitor unit 22 and hold the same for storage or shipping. A coil 24 of a low friction, tubular material is positioned within the shell 11 adjacent to a front wall thereof.

For storing or transporting the borescope 13, the distal end of the insertion tube 14 is inserted into an open proximal end 25 of the coil, and the insertion tube is slidably inserted. The control handle 17, umbilical 19 and connector module 20 are then laid in the case atop the monitor unit 22 after the same has been positioned into the receptacle 23.

As shown in FIGS. 2 and 3, the coil 24 of this embodiment is formed as a flat spiral, this embodiment having two full turns and an additional portion of a turn. The shell 11 has a nominal dimensions of eighteen inches, so the spiral radius is from about 7 to about 8 inches. An insertion tube of up to ten feet in length can be inserted and removed from this coil 24 without difficulty.

In the preferred embodiment as described here, the insertion tube has an outer diameter of about 9 mm, and is covered with a skin of flexible urethane. The coil 24 is formed of PVC tubing having an inside diameter of about 12 to 13 millimeters. As shown in FIGS. 2 and 3, the proximal end portion 25 of the coil can be slightly flared to facilitate insertion of the insertion tube tip. Also, an optional packing 26 can be provided at the distal end of the coil 24 for supporting and cushioning the optics and other delicate instrumentation at the distal tip of the insertion tube.

In the preferred embodiment of the case, aluminum dividers or partitions 27 define the receptacle 23 for the video monitor unit 22. This avoids the need for foam for positioning and storing the unit 22. The partitions 27 and shell 11 also define exhaust air channels 28 so that cooling air can escape if the module 10 is employed while still within the case 10. Because heat-retaining foam, which is employed in other conventional cases, is avoided here, heat dissipation problems are also avoided.

Figure 4:
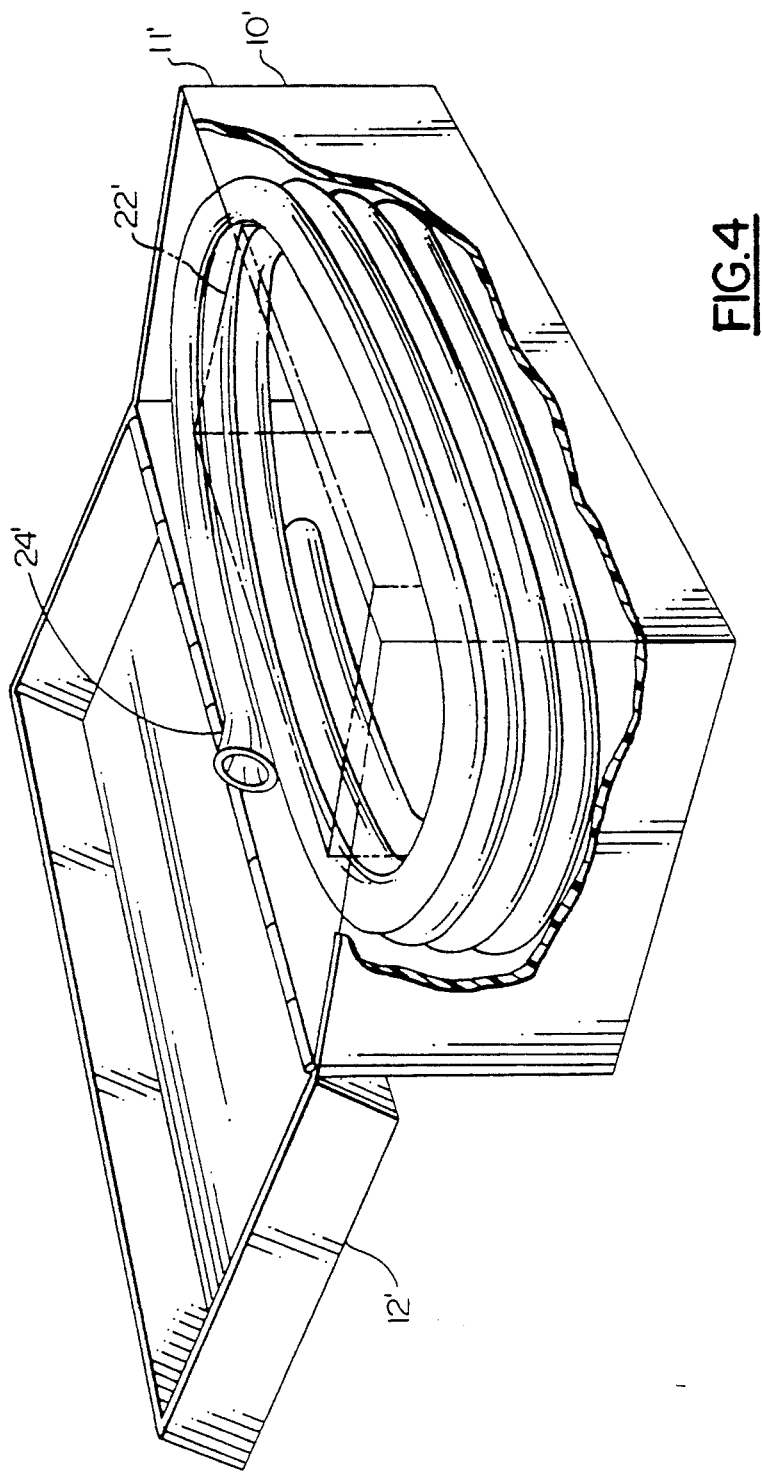
FIG. 4 is a perspective view, partly cut away, of an alternative embodiment of this invention.

FIG. 4 illustrates another alternative embodiment of a case 10' according to this invention, but in which the coil 24' is in the form of a helical spiral 24' disposed adjacent the side walls of the shell or housing 11'. Here, one of the large sides serves as a lid 12'. A central open area defined within the helix 24' can be used for storage of the monitor unit 22' (here shown in ghost lines) and other equipment.

While this invention has been described in detail with reference to certain preferred embodiments, it should be understood that the invention is not limited to those embodiments. For example, other materials could be used for the coils 24, 24', such as metal tubing with a low-friction inner coating. The coil can be mounted on the exterior of a case. Also, the storage system of this invention can be employed with other flexible probes, such as an ultrasonic device or a working tool.

Many modifications and variations are possible without departing from the scope and spirit of the invention as defined in the claims.

What is claimed is:

1. In combination, a borescope or endoscope which has an elongated flexible insertion tube that carries imaging optics at a distal end thereof; and a shipping and storage case for said borescope or endoscope comprising an enclosure for housing the borescope or endoscope, and a coil of tubular low friction material fixedly installed within the enclosure and having an open proximal end into which said insertion tube can be slidably received for storage and from which the insertion tube can be slidably withdrawn without removing the coil of tubular material from the enclosure.

2. The combination of claim 1 wherein said low friction material is PVC tubing.

3. The combination of claim 1 wherein said coil is in the form of a flat spiral positioned adjacent one side wall of the enclosure.

4. The combination of claim 1 wherein said coil is in the form of a helical spiral positioned adjacent side walls of the enclosure.

5. The storage case of claim 1 wherein said insertion tube has a predetermined outer diameter and said tubular low friction material has an inner diameter about 30 to 50 percent greater than the insertion tube outer diameter.

6. The storage case of claim 1 wherein said tubular low friction material is a synthetic polymer tube having an inner diameter on the order of 12 millimeters.

7. A shipping and storage case for a borescope or endoscope which has an elongated flexible insertion tube that carries imaging optics at a distal end thereof; the case comprising an enclosure for housing the borescope or endoscope, and a coil of tubular low friction material positioned within the enclosure and having an open proximal end formed of said low friction material, into which the insertion tube can be slidably received for storage, wherein said coil has said proximal end flared out to increase in diameter gradually so as to facilitate insertion of said insertion tube.

8. A shipping and storage case for a borescope or endoscope which has an elongated flexible insertion tube that carries imaging optics at a distal end thereof; the case comprising an enclosure for housing the borescope or endoscope, and a coil of low friction material positioned within the enclosure and having an open proximal end into which said insertion tube can be slidably received for storage, and wherein the coil has packing means fixedly positioned within its distal end for securely supporting the imaging optics of said insertion tube.

9. A method of storing a borescope or endoscope of the type which has an elongated insertion tube of a predetermined outer diameter and carries imaging optics at its distal end comprising the steps of positioning the distal end of the insertion tube into an open proximal end of a coiled tube that is attached to a storage case having a housing for storing the borescope or endoscope therein, the coiled tube having an inner diameter at least slightly greater than the outer diameter of the insertion tube; and slidably inserting the insertion tube by pushing the insertion tube into said coiled tube.

10. A method of storing a borescope or endoscope of the type which has an elongated flexible insertion tube of a predetermined outer diameter and which carries imaging optics at its distal end; comprising the steps of positioning the distal end of the insertion tube into an open proximal end of a coiled tube that is positioned in a storage case, the coiled tube having an inner diameter at least slightly larger than the outer diameter of the insertion tube; slidably inserting the insertion tube into said coiled tube; and completely enclosing the insertion tube within the storage case after said insertion tube has been fully inserted into said coiled tube.

11. A shipping and storage case for a borescope or endoscope which has an elongated flexible insertion tube that carries imaging optics at a distal end thereof, and a power and illumination unit that attaches to a proximal end of the insertion tube; said case comprising an enclosure for housing the borescope or endoscope and including at least one partition in said enclosure that defines a compartment for housing the power and illumination unit, and a coil of tubular low friction material positioned within the enclosure and having an open proximal end into which said insertion tube can be slidably received for storage.

12. The storage case of claim 11 wherein said coil is in the form of a flat spiral positioned adjacent one side wall of the enclosure, and said partition is situated between said flat coil and an opposite side wall of the enclosure.

13. A shipping and storage case for a borescope or endoscope which has an elongated flexible insertion tube that carries imaging optics at a distal end thereof, and a power and illumination unit that attaches to a proximal end of the insertion tube; said case comprising an enclosure for housing the borescope or endoscope therein including the power and illumination unit, and a coil of tubular low friction material in the form of a helical spiral positioned within the enclosure adjacent side walls of the enclosure, said helical spiral coil having an open core that defines a compartment therewithin for said power and illumination unit, said hleical spiral coil having an open proximal end into wh ich said insertion tube can be slidably received for storage.

* * * * *

UNITED STATES PATENT AND TRADEMARK OFFICE
CERTIFICATE OF CORRECTION

PATENT NO. : 5,314,070
APPLICATION NO. : 07/991135
DATED : May 24, 1994
INVENTOR(S) : Joseph A. Ciarlei It is certified that error appears in the above-identified patent and that said Letters Patent is hereby corrected as shown below:

Column 4, Line 35. Please delete the word "the" and insert the word --said--.
Column 4, Line 42. Please delete the word "end" and replace with --end;--.
Column 4, Line 47. Please delete the word "greater" and insert the word --larger--.

Signed and Sealed this

Twelfth Day of June, 2007

JON W. DUDAS
*Director of the United States Patent and Trademark Office*